(12) United States Patent
Sheardown et al.

(10) Patent No.: US 9,980,545 B2
(45) Date of Patent: *May 29, 2018

(54) CONTACT LENS CASE WITH PREDETERMINED LIFE SPAN FOR SAFETY

(71) Applicant: The Compliance Case Corporation, Toronto, Ontario (CA)

(72) Inventors: Heather Sheardown, Nobleton (CA); Lyndon Jones, Waterloo (CA); Joshua Ellis Josephson, Toronto (CA); Raymond Myers, Collinsville, IL (US)

(73) Assignee: The Compliance Case Corporation, Toronto, Ontario (CA)

(*) Notice: Subject to any disclaimer, the term of this patent is extended or adjusted under 35 U.S.C. 154(b) by 0 days. days.

This patent is subject to a terminal disclaimer.

(21) Appl. No.: 15/207,455

(22) Filed: Jul. 11, 2016

(65) Prior Publication Data

US 2017/0006984 A1    Jan. 12, 2017

Related U.S. Application Data

(60) Continuation-in-part of application No. 14/021,882, filed on Sep. 9, 2013, now Pat. No. 9,387,272, which is a division of application No. 12/916,155, filed on Oct. 29, 2010, now Pat. No. 8,550,238.

(60) Provisional application No. 61/256,076, filed on Oct. 29, 2009.

(51) Int. Cl.
*A45C 11/00* (2006.01)
*A61L 12/08* (2006.01)

(52) U.S. Cl.
CPC .......... *A45C 11/005* (2013.01); *A61L 12/086* (2013.01); *Y10T 29/49826* (2015.01)

(58) Field of Classification Search
CPC ....... A45C 11/005; A61L 12/00; A61L 12/086
See application file for complete search history.

(56) References Cited

U.S. PATENT DOCUMENTS

| 995,415 A | 6/1911 | Steel |
| 2,326,771 A | 8/1943 | Eidson |
| 3,705,659 A | 12/1972 | Mackie |
| 3,772,139 A | 11/1973 | George |
| 4,451,381 A | 5/1984 | Heiss et al. |
| 4,931,488 A | 6/1990 | Chiquet |

(Continued)

FOREIGN PATENT DOCUMENTS

| CN | 201099443 Y | 8/2008 |
| CN | 201337650 Y | 11/2009 |

(Continued)

OTHER PUBLICATIONS

International Search Report, International Patent Application No. PCT/US2010/054818, dated Jul. 28, 2011, 11 pages.

*Primary Examiner* — Mathieu Vargot
(74) *Attorney, Agent, or Firm* — Lewis Rice LLC

(57) ABSTRACT

A contact lens storage case of limited life and predetermined usage to further the safe and effective use of contact lenses by ensuring patient compliance through both limiting case use over a set period of time and discouraging reuse and topping-off of the disinfecting and storage solution. Generally, the self-destruction consists of the case developing a leak in a pre-determined fashion as a result of the change in properties of a material in a limited area of the case following exposure of the case to the storage solution.

20 Claims, 13 Drawing Sheets

(56) References Cited

U.S. PATENT DOCUMENTS

| | | |
|---|---|---|
| 4,956,156 A | 9/1990 | Kanner et al. |
| 4,976,693 A | 12/1990 | Haast |
| 5,178,469 A | 1/1993 | Collinson |
| 5,238,134 A | 8/1993 | Knapp |
| 5,346,929 A | 9/1994 | Guttag |
| 5,633,835 A | 5/1997 | Haas et al. |
| 5,988,426 A | 11/1999 | Stern |
| 6,218,189 B1 | 4/2001 | Antonoplos et al. |
| 6,258,117 B1 | 7/2001 | Camrud et al. |
| 6,323,307 B1 | 11/2001 | Bigg et al. |
| 6,382,408 B1 | 5/2002 | Bruun-Jensen |
| 6,758,338 B2 | 7/2004 | Lien |
| 8,550,238 B2 * | 10/2013 | Josephson ............ A45C 11/005 134/901 |
| 9,387,272 B2 * | 7/2016 | Josephson ............ A45C 11/005 |
| 2003/0116575 A1 | 6/2003 | Ellingson et al. |
| 2005/0033229 A1 | 2/2005 | Scott |
| 2005/0220882 A1 | 10/2005 | Pritchard et al. |
| 2006/0153056 A1 | 7/2006 | Bakos et al. |
| 2006/0213784 A1 | 9/2006 | Tokarski et al. |
| 2008/0073239 A1 | 3/2008 | Duffield et al. |
| 2008/0272009 A1 | 11/2008 | Coon |
| 2008/0296196 A1 | 12/2008 | Duffield et al. |
| 2009/0221891 A1 * | 9/2009 | Yu ...................... A61B 5/14532 600/365 |
| 2009/0272769 A1 | 11/2009 | Contreras et al. |
| 2010/0021534 A1 | 1/2010 | Duffield et al. |
| 2010/0096395 A1 | 4/2010 | Miller |

FOREIGN PATENT DOCUMENTS

| | | |
|---|---|---|
| JP | 11196919 A | 7/1999 |
| JP | 2003038229 A | 2/2003 |
| WO | 9631287 A1 | 10/1996 |

* cited by examiner

Long Case

Separate Base

CONTACT LENS CASE WITH PREDETERMINED LIFE SPAN FOR SAFETY

CROSS REFERENCE TO RELATED APPLICATION(S)

This Application is a Continuation-In-Part (CIP) of U.S. Utility patent application Ser. No. 14/021,882, filed Sep. 9, 2013 and now U.S. Pat. No. 9,387,272, which is a Divisional of U.S. Utility patent application Ser. No. 12/916,155, filed Oct. 29, 2010 and now U.S. Pat. No. 8,550,238, which in turn claims the benefit of U.S. Provisional Patent Application Ser. No. 61/256,076, filed Oct. 29, 2009 and now expired. The entire disclosure of all the above documents is herein incorporated by reference.

BACKGROUND OF THE INVENTION

1. Field of the Invention

This disclosure is related to the field of storage containers for contact lenses. More particularly, this disclosure relates to storage containers for contact lenses that are designed to indicate to a user when the contact lens container has reached the end-point of safe utilization and, therefore, must be replaced.

2. Description of Related Art

The contact lens is a corrective, cosmetic or therapeutic lens which is placed on the cornea of the human eye by a user. Soft hydrogel contact lenses have been available since the early 1970s, when the Czech chemist Otto Wichterle and his assistant Drahoslav Lim developed the first gel utilized in their production. Prior to the development of the soft hydrogel contact lens, the hard contact lens was the standard. This lens was made of rigid polymethyl methacrylate ("PMMA" or "Perspex/Plexiglas"). Some of the disadvantages of the hard PMMA lenses were: 1) that no oxygen was transmitted through the lens to the cornea, which could result in a number of adverse clinical effects; and 2) the long period of adaptation required before a comfort level for the user wearing the lens was achieved.

These problems of oxygen permeability and comfort are not associated with soft contact lenses, which are oxygen-permeable and are able to achieve immediate comfort for a user without a period of adaptation. Because of these inherent advantages, soft contact lenses quickly began to be prescribed to patients more often than hard contact lenses and became the predominant contact lens in the market—a position still held today.

The first generation of soft contact lenses were developed from polymer materials such as poly(hydroxyethyl methacrylate) (polyHEMA). These materials were highly flexible, hydrophilic or "water loving." and compatible with the cornea and conjunctiva. However, despite their hydrophilicity, softness and flexibility, soft contact lenses still had the potential to have deleterious effects on the eye due to the possible interaction of microbes and toxic materials with the hydrophilic materials which comprised the lenses. Due to this risk, soft contact lenses were placed under the control of the Food and Drug Administration (FDA) when they were introduced into the United States in the early 1970s.

Since the first generation of soft contact lenses, there have been many developments in the field. These include the launch of the first silicone hydrogels in the late 1990s, second generation polymers that utilized the Tanaka monomer, and third generation polymers that utilized siloxy macromers. Each of the new generations of soft contact lenses offered improvements in oxygen permeability, wettability, comfort and clinical performance.

Despite improvements in soft contact lenses over the last twenty-five (25) years, there remain a number of issues that impede soft contact lenses from achieving widespread acceptance, the most paramount being the possibility of lens contamination with pathogenic microorganisms. Based in part on these issues, for the past ten (10) years the number of individuals wearing contact lenses has barely changed, being currently estimated at approximately two (2) percent of the worldwide population (about 125 million worldwide with an estimated 30 million of those located in the United States).

In order to keep the hydrogel materials which comprise a contact lens "soft" and in a hydrated state, they must be stored in a solution when they are not being used. Contact lens users typically have a case to store their current pair of contact lenses in solution when they are not being worn, such as when the user is sleeping. Solutions associated with contact lens care generally function as disinfectants, wetting agents and cleansers. In the early days of soft contact lenses, the storage solution for contact lenses was salt tablets dissolved in purified water to produce a 0.9% saline solution. However, without a disinfectant, this saline storage solution quickly supported bacterial growth, especially when misused. As a result, throughout the initial years of soft contact lenses, the lenses were typically heat disinfected in the saline storage solutions. While effective as a disinfectant, the heating process had numerous negative side effects, often resulting in the proteins from the tear film of the lens (which were absorbed into the lenses) being denatured (or deactivated). Often, these protein residues could not be removed from the lenses. In addition, heat disinfection was destructive to some variations of soft contact lens materials.

Due to the negative side effects associated with the heat disinfection method, it rapidly became apparent that some alternative process for disinfection was required. This led to the development of disinfection systems based on hydrogen peroxide, which were neutralized prior to reinsertion of the lenses onto the ocular surface by a prolonged saline soak. However, the hydrogen peroxide-based disinfection systems, while overcoming some of the negative side effects associated with heat disinfection, also had some major disadvantages associated with their utilization. These systems were complex, expensive and open to user misuse, with users frequently failing to remember to neutralize the lenses prior to insertion, resulting in significant ocular discomfort following reinsertion.

As a result of the negative side effects associated with both heat and hydrogen peroxide disinfection methods, preserved disinfection systems began to be developed in the mid-1970's. The most common preserved disinfection systems were based on chemical preservatives. These systems were initially based on mercurial compounds such as thimerosal or low molecular weight bisbiguanide antiseptics such as chlorhexidine. However, uptake of these mercurial compounds or low molecular weight bisbiguanide antiseptics into the hydrogel materials were high and their subsequent release onto the ocular surface resulted in high numbers of allergic complications for soft contact lens users. As a result, companies sought to develop higher molecular weight disinfectants that had lower uptake and release rates. Solutions which could meet the challenge of killing bacteria on stored lenses while not significantly concentrating in the material or otherwise producing a toxic lens were sought after. This resulted in the development of daily care disinfection regimens based on polyhexamethylene biguanide (PHMB) (e.g., Dymed® by Bausch & Lomb) or polyquaternary compounds such as polyquatemium-1 (e.g., Polyquad® by Alcon). More recently, these compounds have been supplemented with other biocides such as alexidine and myristamidopropyl dimethylamine (e.g., Aldox®).

No matter the solution or disinfection method used to store and clean contact lenses, for any user who utilizes contact lenses on a reusable basis, a suitable contact lens case is a necessary component of the contact lens cleansing and storage process. Accordingly, contact lens cases have existed in many forms since the initial stages of contact lens use and play a vital role in the storage, hydration and disinfection of contact lenses. For example, during the era of heat disinfection, contact lens cases needed to be able to withstand heat disinfection. Likewise, in the era of the hydrogen peroxide technique, the case sometimes contained a catalyst which facilitated the breakdown of the hydrogen peroxide. Currently, contact lens cases are often comprised of various plastics including, polyolefin, acrylonitrile butadiene styrene (ABS) and polypropylene designs.

Over the past twenty (20) years, it has become increasingly evident to those of ordinary skill in the contact lens field, that the contact lens case can be a major source for the microbial contamination of contact lenses, which can result in serious corneal infection. Even though many users realize the need to dispose of lenses after the recommended use period, many users do not realize that contact lens storage cases also have a limited period of safe and innocuous use. Even when a contact lens case is rinsed out and cleansed each morning after the lenses are removed and placed in a user's eyes, over time contaminants build up and the contact lens case becomes a fertile breeding ground for microbes. Notably, studies have shown that about 30-80% of the contact lens cases taken from asymptomatic lens wearers test positive for various pathogenic organisms including bacteria, fungi and *Acanthamoeba*. These pathogenic organisms attach to the contact lenses stored in the cases and, eventually, find their way onto the ocular surface following reinsertion of the lenses.

Generally, this is because the contact lens case often harbors a glycocalyx or "biofilm" that shelters microbes from the surrounding solution and prevents their adequate disinfection. Among symptomatic patients, up to one hundred percent (100%) end up with pathogenic colonies in their contact lens cases over time. Recent studies have demonstrated the difference in the effectiveness of currently utilized contact lens disinfection solutions to kill planktonic bacteria (i.e., those free in the environment) over sessile cells found primarily in the biofilm that are protected from disinfecting by the biofilm structure. Biofilms develop in contact lens cases from the absence of appropriate case cleaning, infrequent changing of solution, and/or structural breakdown of the case surface.

Accordingly, user compliance with proper contact lens and case disinfection and care is paramount to prevent the contamination of the lenses, storage container or both. While the introduction of multipurpose disinfection solutions has helped to alleviate some of the problems historically associated with inadequate cleaning of both lenses and cases, failure of a user to strictly comply with recommended disinfecting and cleansing techniques is still quite common. One of the reasons for this is that the contact lens cases currently utilized in the art are exclusively under the control of the user, who often cuts corners in contact lens care in order to save money or, simply, due to the careless aspects of human nature. Solution and case manufacturers and the optometrists and other professionals who prescribe the contact lenses and the proper disinfecting, care and cleansing regime have no control over case "misuse" by contact lens users. Misuse by users includes, but is not limited to, users keeping cases too long, reusing solutions designed for only one-time usage, topping-off old solution in the case with new solution, and inadequate cleaning and hygienic maintenance of the cases. All of these instances of misuse by users have been linked to microbial keratitis, one of the most significant complications of contact lens wear which has potentially devastating effects on the eye, including severe vision loss.

While attempts have been made to create contact lens cases that encourage compliant lens and case care regimens, these contact lens cases only employ passive control mechanisms that remind a user to empty the used solution, not to top-off, to adequately clean the case and to throw away the case at the end of its useable life. However, a user has often already been informed of the correct lens and case care regime by their eye care professional and still often chooses to ignore that advice. The problem in contact lens and case care is not a lack of information; rather, it is the human urge to obtain more usable life out of cases and solutions to cut costs or, simply, apathy towards proper lens care. By analogy, most humans know proper tooth care includes flossing once or more per day, but only about ten (10) to forty (40) percent of people floss every day. It is not a lack of knowledge; it is indolence. These problems will generally not be overcome by passive reminders. An active reminder that, beyond simply reminding, prevents a user from exceeding proper lens case use is needed.

Notably, none of these conventional contact lens cases currently provides such an active control mechanism, preventing a user from continuing to use a case after its safe and sterile lifetime and practicing the deleterious habits of reusing solution, topping-off old solution, and inadequate cleaning. While each of these practices might conserve a user's eye care expenses, each of these practices are counterproductive to safe, comfortable and proper lens care. These practices also expose a user to increased risk of eye infection and disease. Warnings of the potential deleterious effects of improper care and education on proper disinfection and cleansing methodologies are simply not enough to impede this practice of cutting corners that is all too common among contact lens users. Thus, there is a need in the art for an active control mechanism which simplifies contact lens care for a user, thus reducing the number of potential pitfalls and curbing the unhealthy and detrimental common "bad practices" associated with contact lens care, use and storage.

SUMMARY OF THE INVENTION

Because of these and other problems in the art, described herein, among other things, is a contact lens storage compartment comprising: a contact lens case; and an aperture and plug system; wherein the aperture and plug system degrades after exposure to fluid over a predetermined period of time rendering the contact lens compartment unusable for liquid storage.

There is described herein, in an embodiment, a method for creating a self-destructible contact lens case, the method comprising: providing a contact lens case with an aperture molded through a wall of at least one compartment of the contact lens case; inserting a plug into the aperture; and placing into the compartment a fluid and a contact lens, wherein contact between the plug and the fluid causes the plug to swell; wherein after the plug swells sufficiently, the plug separates from the aperture and the contact lens case is no longer able to store fluid and contact lenses.

In an embodiment of the method, the plug comprises a polydimethylsiloxane.

In an embodiment of the method, the plug comprises silicone polyethers such as, but not limited to, ethoxylated polydimethylsiloxane.

In an embodiment of the method, the plug further comprises a color changing agent.

In an embodiment of the method, the color changing agent includes a pH indicator.

In an embodiment of the method, the pH indicator is selected from the group consisting of: phenolphthalein and Bromothymol blue.

In an embodiment of the method, at least one of the at least one compartment of the contact lens case further comprises a color changing agent on the surface thereof.

In an embodiment of the method, the color changing agent includes a pH indicator.

In an embodiment of the method, the pH indicator is selected from the group consisting of: phenolphthalein and Bromothymol blue.

There is also described herein in an embodiment, a self-destructible contact lens case comprising: a contact lens case with an aperture molded through a wall of at least one compartment of the contact lens case; a plug inserted into the aperture; and a fluid and a contact lens positioned within the compartment so contact between the plug and the fluid causes the plug to swell over time: wherein after the plug swells sufficiently, the plug becomes permeable to said fluid and the contact lens case is no longer able to store fluid and contact lenses.

In an embodiment the self-destructible contact lens case of claim 11 further comprises a reservoir including a sub-chamber which includes an aperture, the reservoir being attached to the contact lens case so that the aperture molded through the wall is in fluid communication with the aperture in the sub-chamber.

In an embodiment of the self-destructible contact lens case, the plug comprises a silicone polyether.

In an embodiment of the self-destructible contact lens case, the silicone polyether is ethoxylated polydimethylsiloxane.

In an embodiment of the self-destructible contact lens case, the plug further comprising a color changing agent.

In an embodiment of the self-destructible contact lens case, the color changing agent includes a pH indicator.

In an embodiment of the self-destructible contact lens case, the pH indicator is selected from the group consisting of: phenolphthalein and Bromothymol blue.

In an embodiment of the self-destructible contact lens case, at least one of the at least one compartment of the contact lens case further comprises a color changing agent embedded in a polymer placed thereon.

In an embodiment of the self-destructible contact lens case, the color changing agent includes a pH indicator.

In an embodiment of the self-destructible contact lens case, the pH indicator is selected from the group consisting of: phenolphthalein and Bromothymol blue.

In a still further embodiment, there is described a self-destructible contact lens case comprising: a contact lens case with an aperture molded through a wall of at least one compartment of said contact lens case; a plug inserted into said aperture; and a fluid and a contact lens positioned within said compartment so contact between said plug and said fluid causes said plug to swell over time; wherein after said plug swells sufficiently, said plug separates from said aperture and said contact lens case is no longer able to store fluid and contact lenses.

BRIEF DESCRIPTION OF THE DRAWINGS

FIG. 3A provides a side perspective view of the minimal office contact lens flip case. FIG. 3B provides a top perspective view of the minimal office contact lens flip case when the lids are pressed over the compartments.

FIG. 4A provides a perspective view of an embodiment of the disclosed self-destruct minimal contact lens flip case. FIG. 4B provides a perspective view of an embodiment of the disclosed self-destruct multi-compartment contact lens screw case. FIG. 4C provides a perspective view of an embodiment of the disclosed self-destruct single compartment screw case.

FIG. 7A provides for an embodiment of the aperture design of an open hole filled with degradable material which can be used with the self-destruct lens cases described herein. FIG. 7B provides for an embodiment of the aperture design of an open hole covered with a sieve-like structure which can be used with the lens cases described herein.

FIG. 8A shows an assembled perspective view, FIG. 8B shows an exploded view, and FIG. 8C shows a sectional cut-through view.

DESCRIPTION OF THE PREFERRED EMBODIMENT(S)

Figure 1:
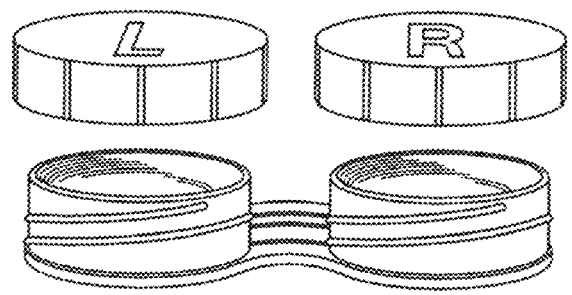
FIG. 1 provides a view of an embodiment of a conventional multi-compartment contact lens screw case with left and right compartments and associated lids.

Described herein, among other things, are contact lens storage cases of limited life and predetermined usage that provide active control mechanisms to further the safe and effective use and care of contact lenses by ensuring patient compliance through both limiting case use over a set period of time and discouraging reuse and topping-off of the disinfecting and storage solution. The disclosed contact lens storage cases will cease useful function at the end of their predetermined or designated lifetime and will be referred to herein as "self-destructing cases" or "self-destruct cases." The self-destruct cases disclosed herein can be used for any and all types of contact lenses known to those of ordinary skill in the art or later discovered, including, but not limited to, hard, gas permeable, scleral, hydrogels, and silicone hydrogel lenses.

The contact lens cases disclosed herein will self-destruct, or become unusable, in a predetermined period of time after their first use in order to reduce the negative effects of bacterial contamination of the case and encourage patient compliance in contact lens care. A "predetermined period of time" as that term is used herein, is a selected window in which the lens case will be destroyed. This window can be a set period of time from initial exposure of the case to fluid (i.e., first use), a set period of time from the manufacture of the case, regardless of variables of fluid exposure, or directly tied to fluid exposure (the longer the exposure to fluid, the shorter the life span).

In general, the "self-destruct" of the contact lens cases defined herein consists of the development of a "leak" in the case in a pre-determined fashion after a specified period of time as a result of a change in the properties of a material in a designated area of the case following exposure of the case to a storage solution used to disinfect and hydrate the contact lens in storage. This leak renders the case unusable as a storage device for contact lens hydration and disinfection. Accordingly, these self-destruct cases can be used to reinforce a manufacturer's and/or professional's suggested care instructions. Contemplated means for self-destruction of the contact lens case described herein include, but are not limited to, chemical, mechanical and electrical aperture and plug systems. In contrast to conventional patient-controlled care regimens, the self-destruct cases place manufacturers and eye care professionals in charge of the case replacement routine, thereby eliminating patient decision making on when the case should be replaced. Generally, the base of the self-destruct case will be similar to conventional contact case designs and features will be added to the conventional designs which establish a fixed period of case use before the time of self-destruction, when the case is rendered unusable.

In one embodiment of the self-destruct contact lens case, the self-destruct contact lens case is comprised of a case for the storage of contact lenses known to those of ordinary skill in the art with an aperture in at least one of the compartment(s) of the case that is filled with a material that initially plugs the hole but, over a defined time period after exposure to a fluid, opens to create a hole or leak in the compartment by shrinkage, expansion, dissolving and/or degradation. This system of self-destruction will be referred to herein as the "aperture and plug" system.

Contemplated substances for the changeable material which comprises the plug include any organic substance which has a partial solubility to fluid and will gradually break-down after initial exposure to a fluid or when exposed to a fluid for a period of time. For example, it can be a matrix, such as collagen, which gradually hydrolyzes or breaks down in the presence of water. Contemplated materials include, but are not limited to, collagen, polysaccharides, and Chitosan-based microcomposites. Notably, certain materials which are contemplated may not actually dissolve, but instead may change their shape through shrinkage, swelling or some other form of shape change. In an embodiment, shrinkage or swelling occur in materials as a result of ions in the fluid which combine with the material thereby changing their form. Further, semi-permeable membranes such as polyurethanes and silicone can be used on surfaces to control the speed of the breakdown material. For the purposes of this application, the whole class of changeable materials known to those of skill in the art that are amorphous or polymeric and have the capability of dissolving, breaking-down or changing shape at a pre-determined rate in the presence of a fluid will be referred to herein as the "degradable materials."

In some embodiments, the degradable materials will only dissolve, degrade or change shape while in the presence of a fluid. The period of time the degradable material is exposed to fluid in these embodiments will inversely correspond to the length of time the plug will remain intact inside the aperture before degradation—the greater the period of time the degradable material of the plug is exposed to a fluid, the shorter the life span of the case. These embodiments have the additional benefit of either allowing the compartment(s) to dry by emptying the compartment and allowing it to be exposed to air or placing the case upside down and doing the same. For example, a daily wear contact lens user generally stores their contact lenses in a case overnight, for approximately eight (8) hours per night. By extension, a self-destruct contact lens case with the aperture and plug system which is designed to last one month could be able to withstand approximately 240 hours of exposure (30 days×8 hours) to a fluid prior to self-destruction. A non-compliant user who failed to empty the case between storage sessions would have a case that lasted much less than one month because of the increase in hours of fluid exposure per day. For example, if the user never emptied his case and fluid was always located in the case compartments the case would only last about eight (8) days. This property directly ties the lifespan of the case to the potential exposure of the case to contamination (which is heightened during periods when fluid is stored therein, reused and not washed out). Further, this practice encourages drying of the case, which reduces bacterial growth, and storage of the case with the lids removed and the openings of the compartment upside-down will force contact lens case to remain open and without contamination.

In alternative embodiments, degradation or shape change of the degradable material will be activated upon initial exposure to fluid and may continue on with or without fluid in the compartment depending on the embodiment. The degradation or shape change in these embodiments is not correlated to direct exposure to fluid after the first exposure. No fluid exposure is required after the initial exposure.

Once the degradable material that plugs the aperture degrades or changes shape to create an opening in the aperture, the compartment(s) of the case can no longer hold contact lens solution and, therefore, contact lenses can no longer be stored therein. Effectively, once the hole in the compartment(s) "opens" the container has self-destructed and is no longer able to function as a contact lens case—it cannot hold the solution required to keep the lenses hydrated during storage. Rather than staying in the compartment, the fluid flows from the compartment of the case through the aperture to the outside of the case.

In alternative embodiments of the aperture and plug system, more than one aperture and plug system is located in the compartment(s) of the contact lens case. Each of these aperture and plug systems can have the same predetermined life span, or different predetermined lifespans to encourage proper care compliance. For example, in one embodiment, an aperture and plug system with a shorter life span will be located in the base of the well (where fluid can sit if the case is not properly emptied) and an aperture and plug system with longer lifespan will be located in the wall of the compartment of the contact lens case. It is also contemplated that, in some embodiments, the aperture and plug system is only located in one of the compartments of the contact lens case when the case has more than one compartment.

While a chemical reacting agent is disclosed herein as the effectuating mechanism of the aperture and plug case, it should also be noted that electrical or mechanical triggers are also contemplated as active release mechanism. In these embodiments, the electrical or mechanical trigger will activate at the end of a predetermined life period, opening the aperture to create a channel of ingress and egress from the compartment.

Figure 2:
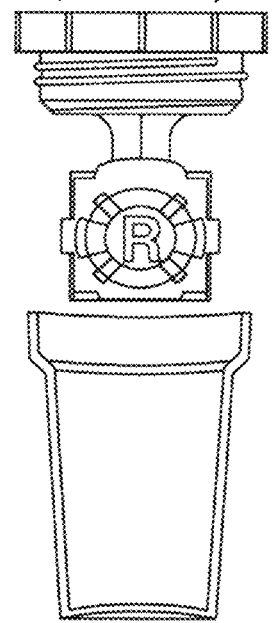
FIG. 2 provides a view of an embodiment of a conventional contact lens screw case with a single compartment.
Figure 3A:
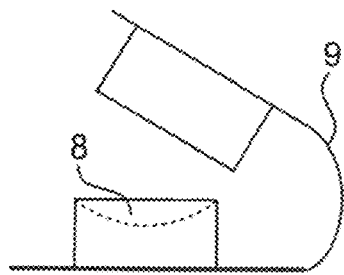
FIGS. 3A and 3B provides a view of an embodiment of a conventional minimal contact lens flip case and lids.
Figure 3B:
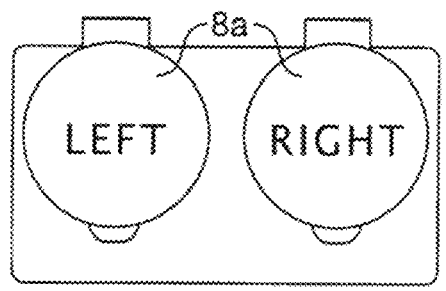
Figure 7A:
FIGS. 7A and 7B provide depictions of several different embodiments of the aperture designs for the disclosed self-destruct contact lens cases.
Figure 7B:
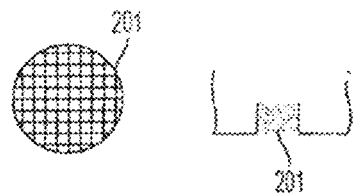

This aperture and plug system for self-destruction of the contact lens case can be implemented in any of the contact lens cases currently used in the art including, but not limited to, the single compartment case (an embodiment of which is provided in FIG. 2), the multi-compartment case (an embodiment of which is provided in FIG. 1) and the minimal office flip contact case (an embodiment of which is provided in FIGS. 3A and 3B). It is contemplated that the aperture and plug system for self-destruction can be implemented into pre-manufactured contact lens cases via drilling or another method that creates a hole in the existing compartment(s) of the case. It is also contemplated that the aperture and plug system for self-destruction can be molded or constructed as part of the case through during the manufacturing process. FIG. 7A provides a view of different embodiments of the structure of the aperture and plug self-destruct system. In one embodiment of the aperture and plug self-destruct system, depicted in FIG. 7B, a sieve or filter (201) is located internally at a position within the internal length of the aperture, generally covering a portion of the internal area of the aperture. The surface area of the sieve or filter (201) is then covered with a thickness of degradable material, thereby creating a plug. This embodiment of the plug has the benefit of imparting additional stability to the plug.

Figure 4A:
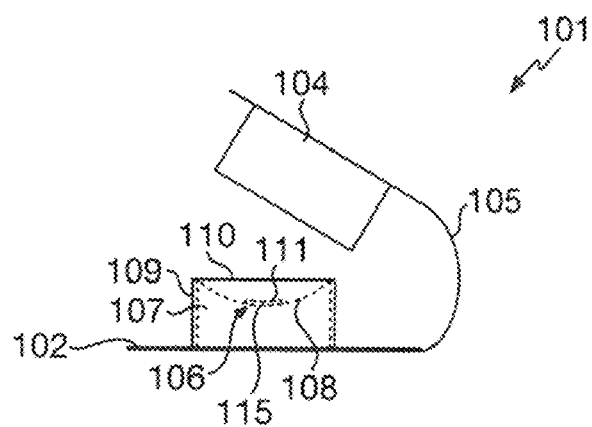
FIGS. 4A, 4B, and 4C provide an embodiment of the disclosed self-destruct contact lens case.
Figure 4B:
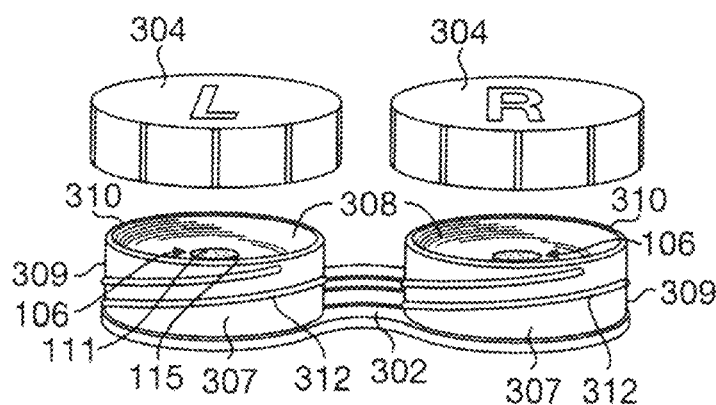

FIG. 4B provides an embodiment of a screw self-destructive contact case (301) wherein the "self-destruct" of the case comes about by an aperture and plug system (106). In this embodiment, the basic structure of the screw self-destructive contact case (301) is generally similar to that of the conventional screw contact case known to those of ordinary skill in the art. The screw self-destructive contact case (301) is comprised of a flat bridge (302), two compartments (307), and two lids (304). The bridge (302) and the two compartments (307) are attached to each other to create a unitary member. The bridge (302) is generally flat and extends between the two compartments (307). The compartments (307) are comprised of a well (308) and a wall (309) rising above the well (308) and ending in a top rim (310), the well (308), the wall (309) and the top rim (310) together defining the exterior bounds of the compartments (307), thus creating a space in which fluid can be stored. Generally, the top rim (310) defines the opening to the compartments (307). The compartments (307) may be sealed by screwing lids (304) onto the compartments (307). The compartments (307) have engagement threads (312) on their exterior surface which engage with inner engagement threads located on the inner surface of the lids (304). This screw interaction secures the lids (304) to the compartments (307), thus forming a seal.

FIG. 4A provides an embodiment of a minimal flip self-destructive contact case (101) wherein the "self-destruct" of the case comes about by an aperture and plug system (106). A minimal flip self-destructive case would be particularly useful when used as an overnight case and leakage after one storage would force one-time use of the case. In this embodiment, the basic structure of the minimal flip self-destructive contact case (101) is generally similar to that of the conventional minimal flip case known to those of ordinary skill in the art. The minimal flip self-destructive contact case (101) is comprised of two compartments (107), each compartment (107) having a well (108) and a wall (109) rising above the well (108) and ending in a top rim (110), the well (108), the wall (109) and the top rim (110) together defining the exterior bounds of the compartment (107), thus creating a space in which fluid can be stored. Extending outward from the compartments (107) is a base (102) that provides stability. Lids (104) that snap on to each of the respective compartments (107) to create a generally leak-free closure are connected to the base (102) or the compartments (107) by flexible straps (105).

Figure 4C:
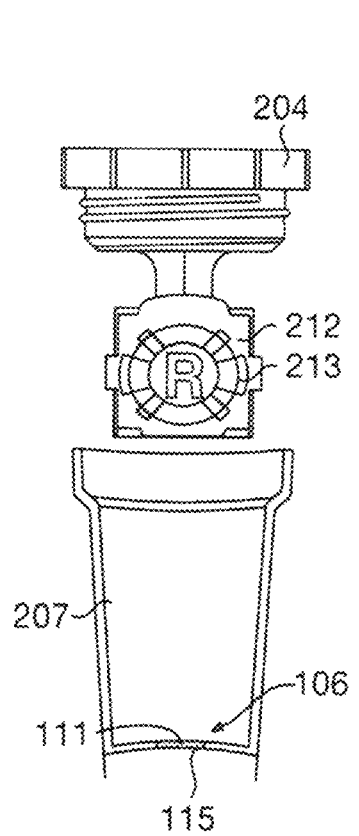

FIG. 4C provides an embodiment of a single compartment self-destruct contact case (201) wherein the "self-destruct" of the case (201) comes about by an aperture and plug system (106). In this embodiment, the basic structure of the single compartment self-destruct contact case (201) is generally similar to that of the conventional single compartment contact case known to those of ordinary skill in the art. The single compartment self-destruct contact case (201) is comprised of a compartment (207), a lid (204) and a contact lens holder (212) with two closable baskets or cages (213) into which the contact lenses are placed in storage. The closable baskets (213) are attached to the contact lens holder (212) which is attached to the underside of the lid (204) such that when the lid (204) is screwed or snapped onto the top of the compartment (207) the baskets (213) are located in the internal area of the compartment (207) and submerged when a solution is present within the compartment (207).

At least one aperture and plug self-destruct system (106) is located in each of the compartments (107) (207) (307) of the cases (101) (201) (301). The aperture and plug system (106) is comprised of an aperture or hole (115) blocked by a plug (111) in each of the compartments (107) (207) (307). The location of this aperture (115) in the compartments (107) (207) (307) is not determinative; the aperture (110) can be located anywhere in the well (108) (208) or wall (107) (207) of the compartments (107) (207) (307). All that is required is that the aperture (115) be a channel from the internal area of the compartments (107) (207) (307) where fluid is stored to outside the compartments (107) (207) (307) such that, when the degradable material degrades or dissolves and the aperture (115) "opens" the compartments (107) (207) (307) are no longer self-contained and fluid can no longer be stored therein.

In addition, the diameter of the plug (111) is not determinative. Any diameter plug that allows for the "plugging" of the aperture and prevents fluid from escaping the compartments pre-degradation and, post-degradation, allows for the egress of fluid from the compartments (107) (207) (307) through the aperture (115) is contemplated. In one embodiment, the aperture (110) will be a diameter of about 2-6 millimeters.

The plug (111) of the case (101) (201) (301) is comprised of a degradable material designed to shrink, expand, dissolve or degrade over a specified period of time after initial exposure to a fluid or in the presence of a fluid. The plug (111) is located within the aperture (115) and, initially, is generally equal in diameter to the thickness of the aperture (115) such that it plugs the aperture (115) and prevents any liquid or fluid from escaping through the channel of ingress and egress created by the aperture (115). The material properties of the degradable substances which comprise the plug (111), along with the radius and/or length of the plug (111), can be varied to manipulate the breakdown or "self-destruct" rate of the plug (111) and, by extension, the life span of the case (101) (201) (301). As such, the volume, surface area or the degradable material comprising the plug (111) can be manipulated to control the predetermined lifespan of the case (101) (201) (301), for example, from as little as one (1) day to, potentially, as long as six (6) months, or any other time period recognized for safe use of the case (101) (201) (301) by the manufacturer or an eye care professional.

In each of the self-destruct contact lens cases depicted in FIGS. 4A through 4C, in the embodiments in which the aperture and plug system is molded into the case during manufacturing, it is contemplated in some embodiments that the cases will be sealed individually within a dry atmosphere by the manufacturer for storage, transport and sale. Accordingly, generally a user's first usage of the case will become the initial exposure of the case to the contact lens solution and, thereby, the starting point of degradation. In another embodiment of the self-destruct contact lens case, the degradable material of the aperture and plug system is kept away from the compartment(s) in which the contact lenses are stored. In this embodiment, the aperture and plug system is located in a secondary compartment such that the aperture and plug system and the degradable materials do not come into contact with the compartment(s) in which the contact lenses are stores. This self-destruct contact lens case is comprised of a case for the storage of contact lenses known to those of ordinary skill in the art (such as the single compartment, screw compartment or minimal office embodiments previously described) with the addition of a secondary drainage compartment in which the aperture and plug system is located and a one-way valve between the contact compartment(s) and the drainage compartment which allows fluid to flow in a one-way direction from the lens compartment to the drainage compartment and keeps the degradable material of the aperture and plug system away from the contact lens compartment(s) in which the contact lenses are stored.

Figure 5A:
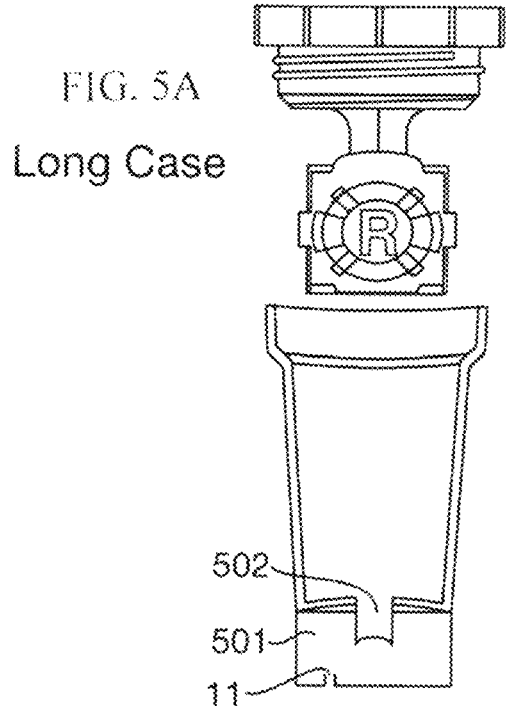
FIG. 5A provides a view of an embodiment of the disclosed self-destruct single compartment screw case with a drainage compartment.
Figure 5B:
FIG. 5B provides a view of the drainage compartment of the disclosed self-destruct single compartment screw case.
Figure 6A:
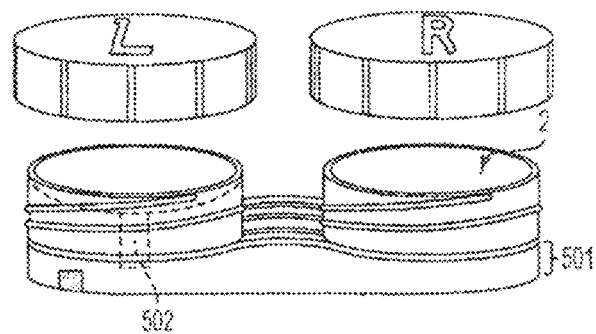
FIG. 6A provides a view of an embodiment of the disclosed self-destruct provides an embodiment of the disclosed self-destruct screw case with a drainage compartment.
Figure 6B:
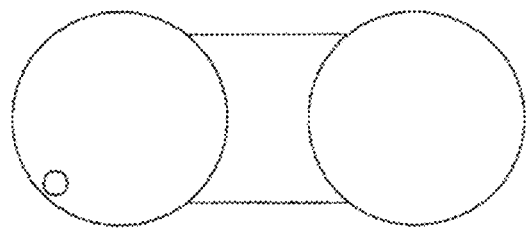
FIG. 6B provides a view of the drainage compartment of the disclosed self-destruct screw case.

FIGS. 5A, 5B, 6A, and 6B provide views of different embodiments of the self-destruct contact lens case in which the aperture and plug system and degradable material is located in a drainage compartment (501), away from the compartment(s) in which the contact lenses are stored. FIGS. 6A through 6B provide a view of an embodiment of the self-destruct screw case with a drainage compartment and FIGS. 5A through 5B provide different views of an embodiment of the self-destruct single compartment screw case with a drainage compartment. In both of these embodiments, the self-destruct case is removed from its sealed, dry packaging or encasement and is activated when the user fills the container with disinfection solution. Generally, the user will be instructed to fill the case to a full level in its initial use since a measured amount will flow into the drainage compartment (501) by way of the one-way valve (502) until the additional compartment becomes full. In some embodiments, two lines will distinguish the initial "full" level from the ordinary level that just covers the contact lens for the purposes of ease of application for the user.

Generally, the valve (502) of these embodiments will be generally implanted somewhere in the bottom of the contact lens compartment(s), creating a one-way channel between the contact lens compartment(s) and the drainage compartment (501). However, this positioning is not determinative and any positioning or implanting of the valve in the contact compartment(s) which allows for the solution in the contact compartment(s) to flow into the drainage compartment (501) through the valve (502) is contemplated in this application.

Figure 9A:
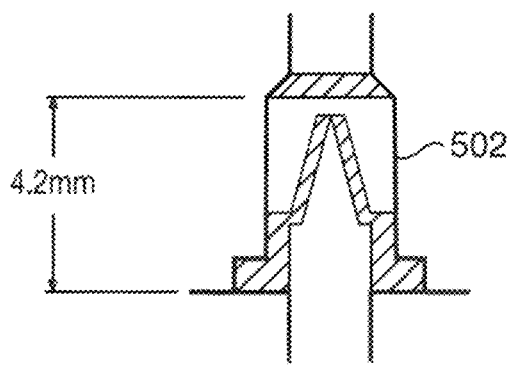
FIGS. 9A and 9B provide for a depiction of an embodiment of one of the valve designs which can be used with the self-destruct lens cases described herein.
Figure 9B:
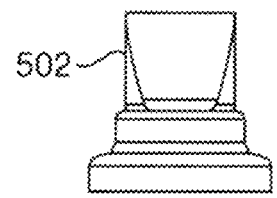

An embodiment of the valve (502) is provided in FIGS. 9A and 9B. The valve (502) generally functions to allow for a one-way transfer of fluid from the contact compartment(s) to the drainage compartment (501). The embodiment of the valve (502) provided in FIGS. 9A and 9B is an elastomeric valve (502) that is 4.2 mm (0.17 in) in size, although it should be noted that this size is not determinative and this application contemplates any sized valve that can be positioned to function as a one-way channel between the contact compartment(s) and the drainage compartment (501). In one embodiment of the valve (502), the valve is a butterfly valve that allows a one-way positive flow out of the contact compartment(s) into the drainage compartment (501) until the drainage compartment (501) is filled and the "butterfly" closes. In an alternative embodiment of the valve (502), the valve (502) is comprised of a ball in a minitube which is in an open position yielding positive flow from the compartment(s), and closes off with backward translation from positive flow from the drainage compartment (501).

In the embodiments of the self-destruct cases with a valve depicted in FIGS. 5A through 6B, upon the insertion of fluid into the contact compartment(s), the fluid will begin to gradually flow through the valve (502) into the drainage compartment (501) in which the aperture and plug system and the degradable material is located. In some embodiments of the self-destruct case with a valve, a venting hole will be located in the contact lens compartment to assist the flow of fluid from the contact lens compartment to the drainage compartment (501). The contact compartment(s) are the source for fluids activating the degradable material in the aperture and plug system located in the drainage compartment (501).

In these embodiments, the aperture and plug system previously described in this application is located in the drainage compartment (501). FIGS. 5B and 6B show a view of the aperture and plug system in the drainage compartment (501). While these FIGS. depict the aperture and plug system in the base of the drainage compartment (501), this location is in no way determinative. It is contemplated that the aperture and plug system in these embodiments may be located anywhere in the walls of the drainage compartment (501) such that it acts as a channel from the interior of the drainage compartment (501) to an area outside the self-destruct contact lens case, thereby rendering the case unusable once the degradable material of the aperture and plug system is no longer plugging the aperture.

In the self-destruct case with a valve, inversion of the case when contact lenses are not stored therein is encouraged to increase the life of the case. As described, fluid drains from the contact compartments to the drainage compartment (501) and the fluid is stored in the drainage compartment (501) where the aperture and plug system is located. As the valve (502) of these embodiments is only a one-way valve (502), when the case is inverted during non-storage periods the fluid in the drainage compartment (501) will be directed to the top of the drainage compartment (501), away from contact with the aperture and plug system. Thus, correct use of these self-destruct cases with valves would require inverting the case during non-storage periods. Failure to invert would increase the fluid exposure period for the aperture and plug system and, by extension, greatly decrease the life span of the case.

Figure 8A:
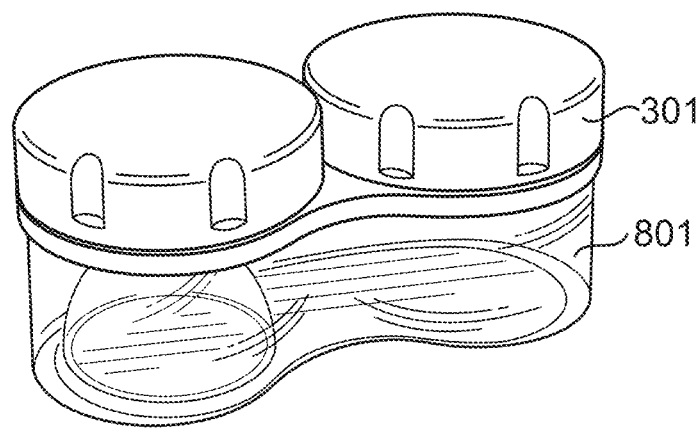
FIGS. 8A, 8B, and 8C provide for various views of another embodiment of a self-destruct contact lens case with a drainage compartment.
Figure 8B:
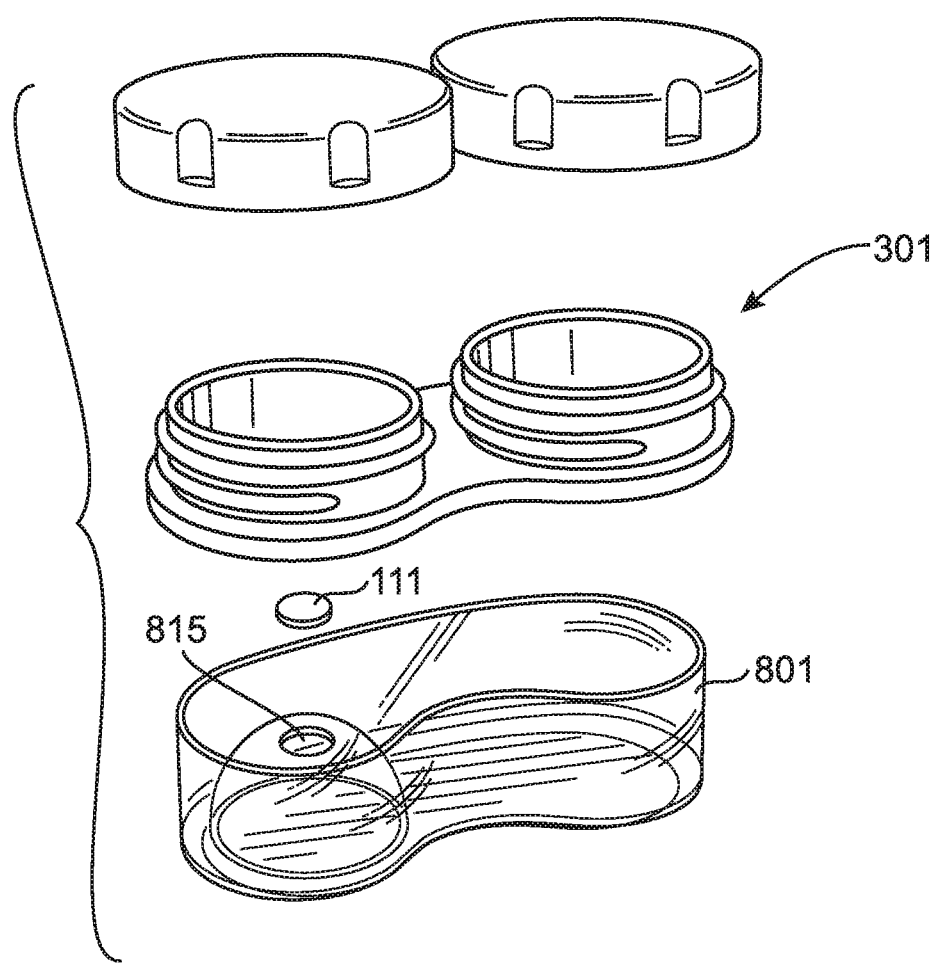
Figure 8C:
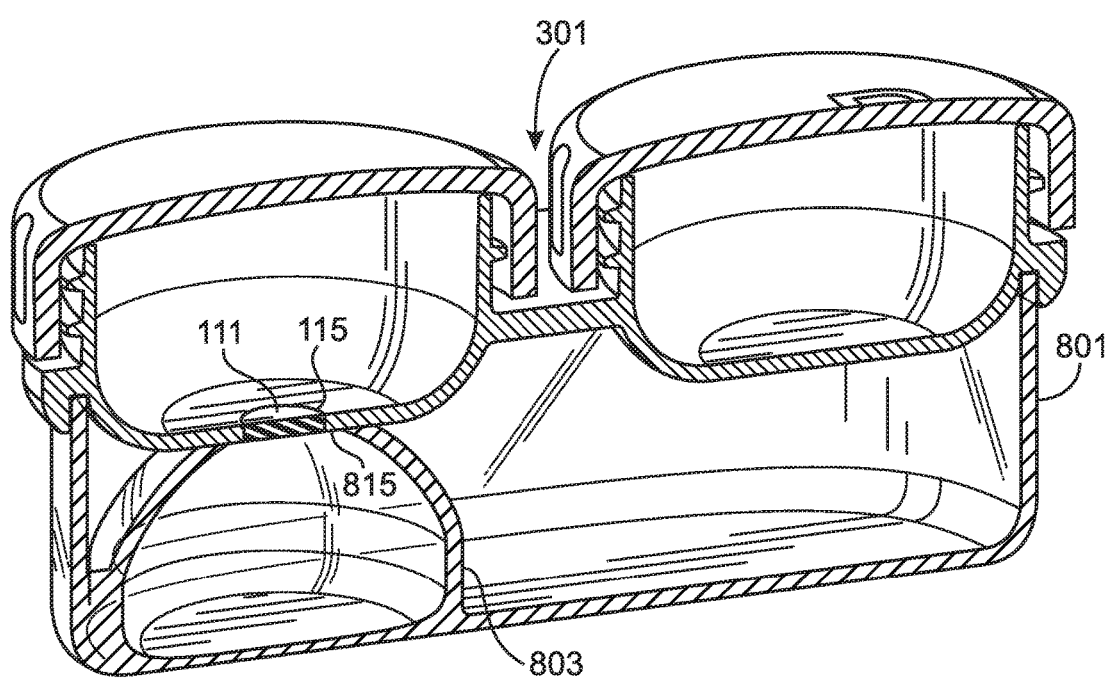

FIGS. 8A through 8C provide for a still further embodiment of a self-destructing contact lens case. In the embodiment of FIGS. 8A through 8C, the case (301) is a screw top case of the type shown in FIG. 4B. The case (301) is however placed over the top of a reservoir (801). The reservoir (801) will generally be bonded to the bottom of the case (301) by an adhesive or other similar material so that it is not readily separable. However, this is not required, and other methods of connection such as snap connections, screw threads, or magnets may be used whether such engagements are intended to be non-separable in normal use or are intended to be separable in normal course. The reservoir (801) may also be co-molded with the case (301) in an embodiment. However, this is generally non-preferred as it is usually preferred that the case (301) and reservoir (801) be constructed of different materials. Specifically, the case (301) will commonly be opaque while the reservoir (801) is transparent.

The reservoir (801) in the depicted embodiment includes a sub-chamber (803) which is connected to the aperture (115) via a top aperture (815) which is best seen in FIG. 8B. The sub-chamber (803) is generally formed entirely within the structure of the reservoir (801) and in the depicted embodiment is in the forms of a parabolic cone but this is by no means required and any shape may be used. The aperture (115) and, thus, the aperture (815) are closed by the plug (111).

Upon plug failure in the embodiment of FIGS. 8A through 8C, the fluid in the lens case (301) will generally pass through the apertures (115) and (815) and into the sub-chamber (803). In an embodiment, the sub-chamber (803) will include a dying, coloring, or similar agent that will react with the contact lens fluid and discolor either the fluid and/or the surfaces of the sub-chamber (803). The presence of fluid in the sub-chamber (803), or the coloration will generally be readily detectable by a human user and can be used as an indication that the case has self-destructed and needs to be replaced.

The use of the sub-chamber (803) is preferred but not required as it provides for an additional level of protection for fluid escape. In the event that the case (301) self-destructs and fluid enters the sub-chamber (803), even if there is a hole in the sub-chamber (803) or if the connection between apertures (115) and (815) is not complete, fluid cannot spill out of the device as a whole. Instead, such lost fluid would simply go into reservoir (801) and be contained.

In order to construct the plug (111) of the various embodiments discussed herein, it should be recognized that plugs can be made which are destroyed via contact with the lens solution in a number of different ways. In a first embodiment carboxymethyl cellulose (CMC) may be combined with polyvinyl acetate (PVA) and poly(vinylpyrrolidone) (PVP) to form a solution. This will create a plug which will dissolve. The concentration of CMC will generally vary depending on how long the plug is intending to last for and various concentrations are provided in FIG. 11 along with the failure time in days. It is important to recognize that contact lens fluids will behave very differently from water or other materials and that a plug failure will only occur if the hole is large enough to result in leakage. Thus, exact composition of the material will generally be developed experimentally. Plugs may then be formed on a silicone encapsulent (polydimethylsiloxane or PDMS) surface such as Sylgard 184 manufactured by Dow Corning and adhered in the aperture (111) using the same encapsulant.

In an embodiment, the PDMS reagents were mixed in a vial in accordance with standard practice. The PDMS mixture was then poured on a 10 mm tissue culture treated petri dish (a non-treated dish is believed to not work). Using a pipette, 1, 2 or 5 microlitres of 0.5 mg/mL CMC solution with PVA and PVP was placed thereon. The structures were then cured overnight at 37° C. with the lid of the petri dish on. The lid is then removed and the plugs kept in the oven for another 24-48 hours until the CMC is completely dry. The optimal volume of wetting agent added was found to be 2 microlitres. Once cured, the PDMS film is slowly peeled from the petri dish and disks are punched so that the dried CMC plugs (111) are in the center. The CMC plugs (111) can then be adhered to the lens case (101), (201), and/or (301) using additional PDMS.

Figure 12:
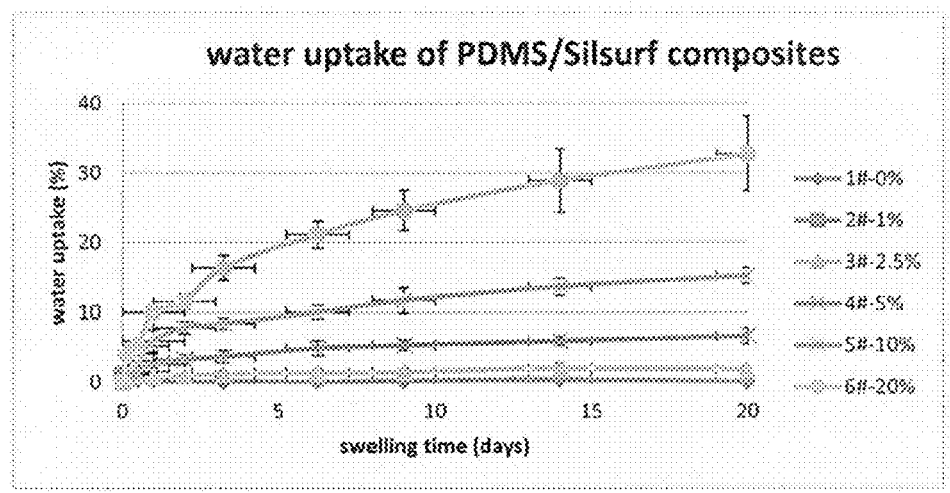
FIG. 12 shows a graph of the water uptake of various PDMS/Silsurf composites for constructing a swelling plug which can pop loose.

In alternative embodiment, plugs (111) may be created which fail by swelling and "pop off" the aperture or which become permeable to the lens fluid after swelling a certain amount. Silicone polyethers such as ethoxylated polydimethylsiloxane which is commonly known as "Silsurf" can regulate PDMS swelling ratio and swelling time. In this approach, different amounts of Silsurf can be added to the PDMS formulation. This can be used alone as a plug or in conjunction with plugs including CMC as contemplated above. The swelling ratio and swelling time can be modified as shown in FIG. 12. The times at which such plugs are no longer adherent to the aperture vary and, in an embodiment, are recorded in Table 1 below.

TABLE 1

| sample # | Silsurf content | Staying time |
|----------|-----------------|--------------|
| 1#       | 0%              | >55 days     |
| 2#       | 1%              | >55 days     |
| 3#       | 2.50%           | >55 days     |
| 4#       | 5%              | >55 days     |
| 5#       | 10%             | 36 days      |
| 6#       | 20%             | 15 days      |

As can be seen in Table 1, a plug including 10% Silsurf can provide a case with reminder time of one month, while the 20% Silsurf containing plug came off after 2 weeks. These marker times can be easily tuned using different content of hydrophilic silicones such as Silsurf.

Whereas the above-described embodiments of self-destruct cases provide cases of a predetermined life span and limited use with varying usage periods, there may be a need in each of the embodiments to have a signaling mechanism to indicate when self-destruction will occur.

Figure 10A:
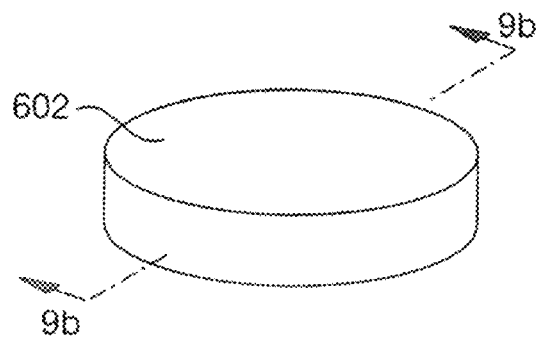
FIG. 10A provides a perspective view of a depiction of an embodiment of a multilayer configuration for use in a multilayer notification plug which can be utilized with the self-destruct lens cases described herein.
Figure 10B:
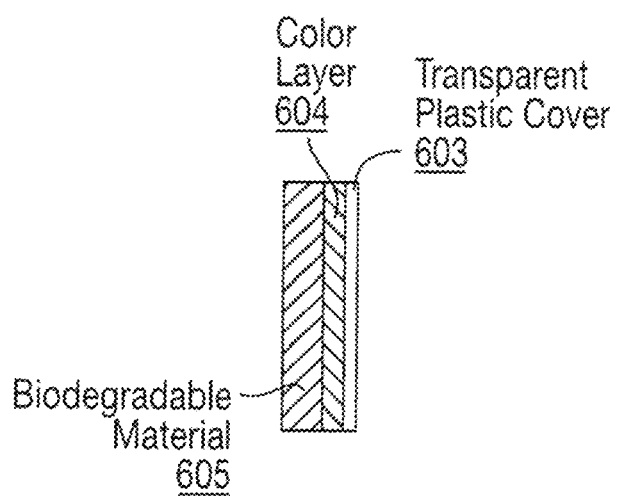
FIG. 10B provides a cut-through of the same embodiment.

Accordingly, in another embodiment, the self-destruct contact lens case is comprised of a case for the storage of contact lenses known to those of ordinary skill in the art with the aperture and plug system previously disclosed in this application, with the addition of a multilayer covering or plug to the aperture and plug system that offers a means of notification to a user if the case is near its eventual self-destruction. FIGS. 10A and 10B provide a depiction of this embodiment of the disclosed self-destruct contact lens case with notification methodologies.

In this embodiment, a second "notification" aperture is created in the compartment of the self-destruct lens case. This aperture can be created during manufacturing through molding or post-manufacturing through a drilling methodology. A multilayer plug (602) is placed in this second "notification" aperture. FIGS. 10A and 10B provide a depiction of this multilayer plug. The multilayer plug (602) is generally a layered plug similar to the plug of the plug and aperture system except instead of degrading to lead to an eventual leak the multilayer plug (602) is constructed such that the degradable material degrades to expose a color sensitive disc. The multilayer plug (602) of this embodiment is generally comprised of three layers. The first layer (603) of the multilayer plug (602) is generally a solid, transparent material (such as plastic in one embodiment) which does not break-down from the contact lens disinfection solution. The first layer (603) is located on the outside-facing portion of the aperture. The second layer (604) of the multilayer plug (602) is the layer of the plug (602) which is located between the first layer (603) in the plug (602) and the third layer (605) of the plug (602). The second layer (604) is generally a compound which turns color in the presence of moisture. In these embodiments, it is contemplated that this additional moisture will be exposed to the second layer (604) close to the end of the life of the case. The third layer (605) of the multilayer plug (602) is the layer of the plug (602) which is exposed to the compartment(s) and the fluid housed therein. The third layer (605) is comprised of the degradable material previously described in this application.

The multilayer plug functions as follows. The third layer (605) is manufactured at a designated thickness such that the third layer (605) will dissolve at a rate faster than the degradable substance of the aperture and plug system. Once the third layer (603) of the multilayer plug (602) has degraded, the fluid in the compartments will be exposed to the second layer (604) resulting in the second layer (604) changing colors to indicate to a user that self-destruction of the case is about to occur. The thickness of the first layer (603) can be manipulated to alter the period of notification. For example, in the signal via color change could occur one week, five days or twenty-four hours prior to self-destruction. Notably, this second "notification" aperture is not intended to have a role in draining the case, but is only contemplated as a signaling method for the user to notify a user when the case is about to self-destruct. In conclusion, the self-destruct contact lens cases disclosed herein provide active control mechanisms through, among other things, the aperture and plug system, which prevent a user from continuing to use a case after its safe and sterile lifetime and practicing poor lens care habits.

The self-destruct contact lens cases disclosed herein also gives manufacturers and eye care professionals more control over the length of time a contact case is used—only cases with a predetermined lifespan mandated by the manufacturer or eye care professional will be manufactured and dispensed. Thus, these cases allow manufacturers and eye care professionals to wield more control in reducing uncontrolled lens storage and preventing the severe complications associated with contact lens cases and solutions. Thus, the self-destruct contact lens cases of this application offer simplification over conventional cases, with assured positive changes to a safe regimen by effectuating: 1) programmed destruction for limited case use; 2) only one use of contact lens solution in the case for each period of storage; 3) drying out the container when contact lenses are not being stored; 4) constructing a case that must be stored inverted and with the lids off; 5) possibility of tying the replacement of contact lenses with period of limited usage of the case; 6) possibility of tying the replacement of an open bottle of contact lens solution with the period of limited usage of the case; 7) designing dual packaging of the contact lens case and a specific bottle size of contact lens solution, to reinforce proper solution use; 8) designing dual packing of frequent replacement contact lenses and their subsequent usage limits with the period of limited usage of the case; and 9) designing the combined packing of frequent replacement lenses, contact lens bottle size with the period of limited usage of the case.

Figure 11:
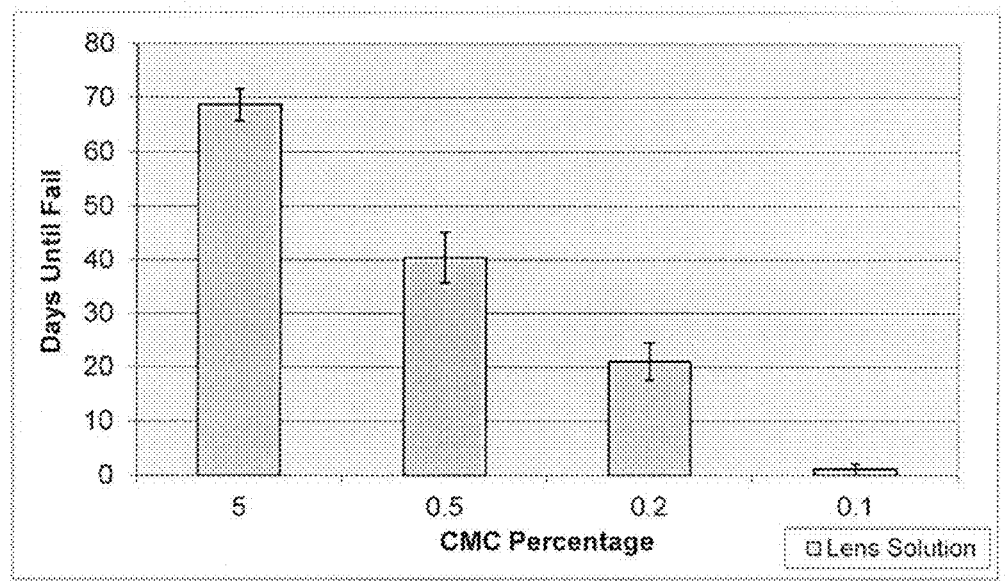
FIG. 11 shows a bar graph of the days to failure for a lens case plug such as that of FIG. 8B depending on percentage of carboxymethyl cellulose (CMC) in the plug structure. These plugs fail by dissolution of structure

In a still further embodiment, the self-destructing aperture can be combined with a color change indicator which may be on a surface of the lens case (101), (201) or (301) or may be combined directly with plug (111) material as contemplated by the discussion in conjunction with FIGS. 11 and 12.

In an embodiment, a Silicone coating, such as is created through the use of PDMS, is loaded with a pretreated pH indicator changes color due to swelling by the lens solution over time. In order to produce a color change when in contact with a lens solution (as opposed to other materials, such as simple water vapor from bathroom humidity or other items), pH indicators can be used to trigger color changes. Suitable pH indicators include, but are not limited to, phenolphthalein (PPT) or Bromothymol blue (BTB). Generally, the pH indicator will be pre-treated using an acid or base so as to provide a material with little or no color. The treated pH indicator is then mixed or otherwise combined with material comprised of PDMS. The indicator incorporated in PDMS shows its color in an acid or base condition depending on the pre-treatment condition. When the coating is exposed to contact lens solution buffer at pH range 6.5-7.5, the buffer will slowly swell the coating material, leading to a color change of the coating after certain predetermined periods of time, determined by the nature of the case coating material and the loading of the indicator. This color change then serves as a visible reminder to the contact lens case user to stop using the case. As discussed above, swelling associated with a color changing activity can also result in a plug including PDMS and a pH indicator to separate from the aperture after a suitable period of time.

As would be understood by one of ordinary skill in the art, different pH indicators can be selected based on color choices and non-toxicity requirement and elements such as dye (pH indicator reagent) concentration, material water swelling ratios (tuned by adding silicone surfactant or other hydrophilic components to the coating material), extra coating on the marking material surface, and different types of dye can be used to control specific color change criteria over time. It is generally preferred that the dye be immobilized in the coating material to prevent its release and the subsequent contamination of lens cleaning solutions which, while likely harmless to the user, could be considered displeasing in appearance.

Various dye coatings have been created and tested for color change as contemplated in the following example:

EXAMPLE

The following chemical reagents were used in contact lens coating preparations: PDMS Sylgard 184 elastomer kit (Dow Corning Corporation, Mi, USA), silicone surfactant, Silsurf 802 (Siltech Corporation, Ontario, Canada), pH indicator dyes including BTB and PPT (Sigma-Aldrich Canada), Tetrahydrofran (THF) as a dispersing agent (Sigma-Aldrich Canada). Contact lens cases used were purchased from Alcon and the contact lens solution used for color change period determination was an OptiFree contact lens solution (Alcon).

25 mg/ml Bromothymol blue (BTB) was dissolved in water (blue color showing), the solution was adjusted to a pH of 2 by adding 2 N HCl. After that, the solution was freeze dried to form an orange colored powder. Acid treated BTB was directly added to Silgard 184 kit or dissolved in THF and then mixed with PDMS kit according to the recipes shown in Tables 2, 3, and 4 as shown later.

Silsurf 802 was added during Silgard 184 formulation mixing step. After allowing silicone kit to degas in air for 30 minutes, one drop (~50 ul) of elastomer kit containing BTB was applied to the bottom of the lens case. The case was transferred to a 60° C. oven and kept for 4-6 hours to allow for complete curing. Three groups of trials were performed to investigate the effect of Silsurf, solvent and extra PDMS coating layer effect on color change time.

The left side chamber of the tested case remained empty as a control, while 2 ml of OptiFree contact lens solution was added to the right chamber of the case. The lens solution was replaced with fresh solution every day and the color changes were checked and photographed as shown in the various referenced FIGS.

Figure 13:
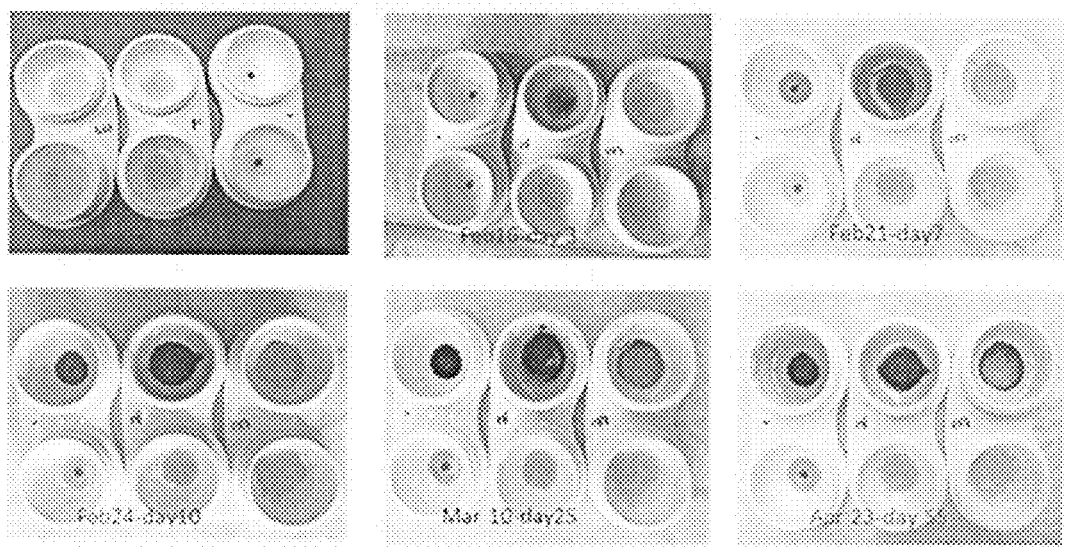
FIG. 13 shows various color changes of a contact lens case in conjunction with Table 2.

As shown in FIG. 13 and Table 2, without the dispersing solvent, the dye was not mixed evenly. Sample #2 indicated that Silsurf triggered release of the dye. 1-1 and 1-2 samples changed color after 10 days of exposure to the contact lens solution. Samples with an extra coating layer (1-3) showed longer duration prior to color change, to periods of more than 1 month.

TABLE 2

Effect of Silsurf and extra coating on color change time.

| Recipe # | Silgard 184 | BTB added | Silsurf 802 added | Extra coating (PDMS only) |
|---|---|---|---|---|
| 1-1 | 2.5 g | 50 mg | N/A | N/A |
| 1-2 | 2.5 g | 50 mg | 250 mg | N/A |
| 1-3 | 2.5 g | 50 mg | 250 mg | 250 mg |

Figure 14:
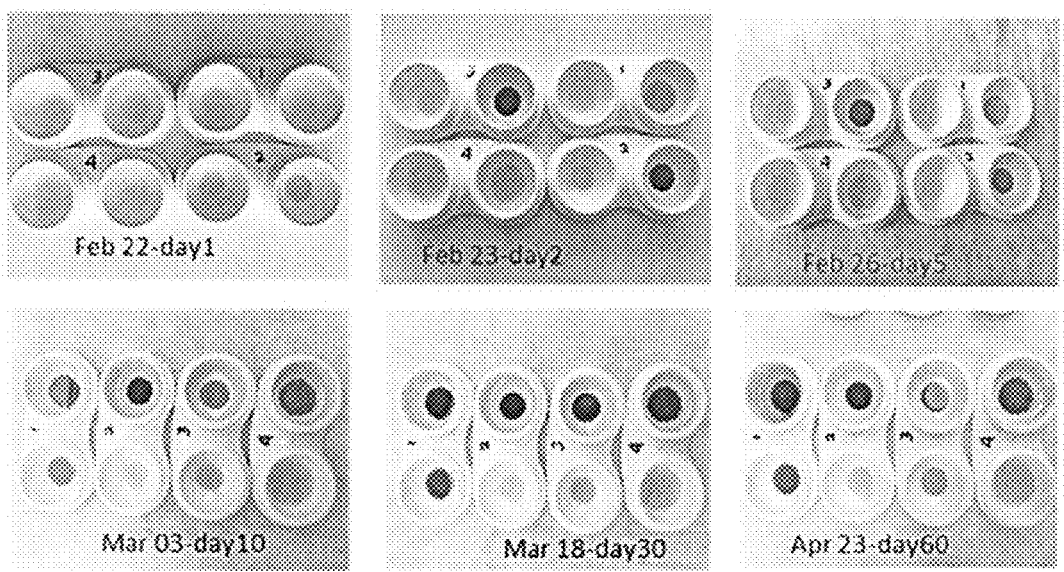
FIG. 14 shows various color changes of a contact lens case in conjunction with Table 3.

As shown in FIG. 14 and Table 3, addition of both THF and Silsurf led to more even dye dispersion, but they also made color change time shorter. As proved in Trial 1, extra coating is an effective method for extending color change time. A color change can be seen at day 2 and became very obvious at day 5 for case 2 and case 3. Case 1 and case 4 showed slight color changes at day 10 and became darker blue at day 30. Although case 1 control color changed after 60 days, the color of the rest of control cases remained orange over the testing period.

TABLE 3

Testing of failure times using 1% BTB and 5% Silsurf

| Recipe # | Silgard 184 | BTB added | Silsurf 802 | THF added | Extra coating (PDMS only) |
|---|---|---|---|---|---|
| 2-1 | 2.5 g | 25 mg | N/A | N/A | N/A |
| 2-2 | 2.5 g | 25 mg | 125 mg | N/A | N/A |
| 2-3 | 2.5 g | 25 mg | N/A | 125 µl | N/A |
| 2-4 | 2.5 g | 25 mg | N/A | N/A | 0.25 ml of Silgard kit |

Figure 15:
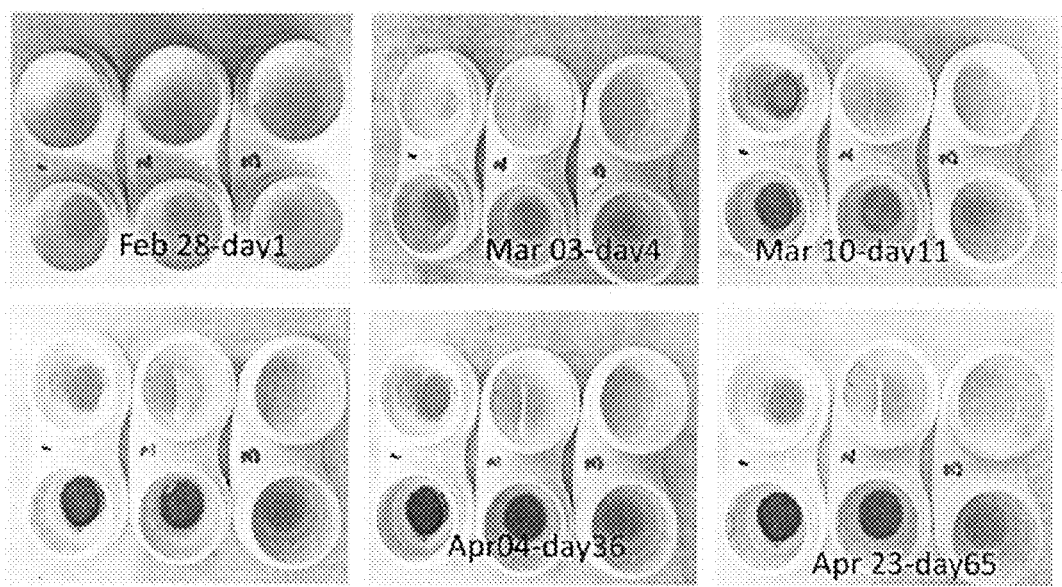
FIG. 15 shows various color changes of a contact lens case in conjunction with Table 4.

To extend color change time, 1% Silsurf and less THF (125 µl per 25 mg BTB) were used in a third trial discussed in conjunction with FIG. 15 and Table 4. In addition, in sample 3-3 the extra coating layer was added and cured after the BTB containing PDMS bottom coating cured. This was expected to provide stronger masking for preventing an early color change due to rapid swelling. As found in FIG. 15, the dye was dispersed evenly and color change time was extended to 1 or 2 months using modified recipes and protocols in the third trial. The color of the control sides was stable over 2 months. Longer term testing has shown that the controls were stable for more than 1 year of shelf life time.

TABLE 4

Recipes to extend color change time by adding less dispersing agent THF

| Recipe # | Silgard 184 | BTB added | THF added | Extra coating (PDMS only) |
|---|---|---|---|---|
| 3-1 | 2.5 g | 25 mg | 50 µl | 0.1 g |
| 3-2 | 2.5 g | 25 mg | 50 µl | 0.2 g |
| 3-3 | 2.5 g | 25 mg | 50 µl | 0.2 g (added after marking PDMS cured) |

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A method for creating a self-destructible contact lens case, the method comprising:
   providing a contact lens case with an aperture molded through a wall of at least one compartment of said contact lens case;
   inserting a plug into said aperture; and
   placing into said compartment a fluid and a contact lens, wherein contact between said plug and said fluid causes said plug to swell;
   wherein after said plug swells sufficiently, said plug becomes permeable to said fluid and said contact lens case is no longer able to store fluid and contact lenses.

2. The method of claim 1, wherein said plug comprises a silicone polyether.

3. The method of claim 2, wherein said silicone polyether is ethoxylated polydimethylsiloxane.

4. The method of claim 1, wherein said plug further comprises a color changing agent.

5. The method of claim 4, wherein said color changing agent includes a pH indicator.

6. The method of claim 5, wherein said pH indicator is selected from the group consisting of: phenolphthalein and Bromothymol blue.

7. The method of claim 1, wherein at least one of the at least one compartment of said contact lens case further comprises a color changing agent on the surface thereof.

8. The method of claim 7, wherein said color changing agent includes a pH indicator.

9. The method of claim 8, wherein said pH indicator is selected from the group consisting of: phenolphthalein and Bromothymol blue.

10. A self-destructible contact lens case comprising:
a contact lens case with an aperture molded through a wall of at least one compartment of said contact lens case;
a plug inserted into said aperture; and
a fluid and a contact lens positioned within said compartment so contact between said plug and said fluid causes said plug to swell over time;
wherein after said plug swells sufficiently, said plug becomes permeable to said fluid and said contact lens case is no longer able to store fluid and contact lenses.

11. The self-destructible contact lens case of claim 10 further comprising:
a reservoir including a sub-chamber which includes an aperture, said reservoir being attached to said contact lens case so that said aperture molded through said wall is in fluid communication with said aperture in said sub-chamber.

12. The self-destructible contact lens case of claim 10, wherein said plug comprises a silicone polyether.

13. The self-destructible contact lens case of claim 12, wherein said silicone polyether is ethoxylated polydimethylsiloxane.

14. The self-destructible contact lens case of claim 10, wherein said plug further comprises a color changing agent.

15. The self-destructible contact lens case of claim 14, wherein said color changing agent includes a pH indicator.

16. The self-destructible contact lens case of claim 15, wherein said pH indicator is selected from the group consisting of: phenolphthalein and Bromothymol blue.

17. The self-destructible contact lens case of claim 10, wherein at least one of the at least one compartment of said contact lens case further comprises a color changing agent embedded in a polymer thereon.

18. The self-destructible contact lens case of claim 17, wherein said color changing agent includes a pH indicator.

19. The self-destructible contact lens case of claim 18, wherein said pH indicator is selected from the group consisting of: phenolphthalein and Bromothymol blue.

20. A self-destructible contact lens case comprising:
a contact lens case with an aperture molded through a wall of at least one compartment of said contact lens case;
a plug inserted into said aperture; and
a fluid and a contact lens positioned within said compartment so contact between said plug and said fluid causes said plug to swell over time;
wherein after said plug swells sufficiently, said plug separates from said aperture and said contact lens case is no longer able to store fluid and contact lenses.

* * * * *